(12) United States Patent
Downing et al.

(10) Patent No.: US 9,370,170 B2
(45) Date of Patent: Jun. 21, 2016

(54) REMOTE MONITORING SYSTEMS

(71) Applicant: ILLINOIS TOOL WORKS INC., Glenview, IL (US)

(72) Inventors: Mark L. Downing, Oakwood Hills, IL (US); Robert L. Pliml, Wheeling, IL (US); Steven S. Spelbring, Appleton, WI (US); Nathan W. Johnson, Kaukauna, WI (US); Kimberly A. Cannon, Neenah, WI (US); Daniel Dina, North Barrington, IL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 13 days.

(21) Appl. No.: 14/360,316

(22) PCT Filed: Nov. 29, 2012

(86) PCT No.: PCT/US2012/066962
§ 371 (c)(1),
(2) Date: May 23, 2014

(87) PCT Pub. No.: WO2013/082227
PCT Pub. Date: Jun. 6, 2013

(65) Prior Publication Data
US 2014/0333439 A1    Nov. 13, 2014

Related U.S. Application Data

(60) Provisional application No. 61/565,357, filed on Nov. 30, 2011.

(51) Int. Cl.
*G08B 23/00* (2006.01)
*A01K 29/00* (2006.01)
(Continued)

(52) U.S. Cl.
CPC .............. *A01K 29/005* (2013.01); *A61B 5/002* (2013.01); *A61B 5/0008* (2013.01); *A61B 5/6817* (2013.01); *A61D 17/002* (2013.01); *G01K 1/024* (2013.01); *G01K 1/026* (2013.01);
(Continued)

(58) Field of Classification Search
CPC . A01K 29/005; A01B 2503/40; G01K 13/004
USPC ......................................... 340/573.3; 600/301
See application file for complete search history.

(56) References Cited

U.S. PATENT DOCUMENTS 4,854,328 A    8/1989  Pollack
6,113,539 A    9/2000  Ridenour
(Continued)

FOREIGN PATENT DOCUMENTS

FR    2801491 A1    6/2001
WO    2005/115242 A2    12/2005

OTHER PUBLICATIONS

ISR for PCT/US2012/066962 mailed Apr. 29, 2013.

*Primary Examiner* — Toan N Pham

(57) ABSTRACT

A system includes sensors for transmitting data on a low power and/or short range transmission link, and one or more coordinators in wireless communication with the sensors. The coordinators convert signals received via the low power and/or short range transmission link to a longer range transmission link. A base station is in wireless communication with the coordinators via the longer range transmission link so that data generated by the sensors is transferred to the base station via the coordinators.

27 Claims, 4 Drawing Sheets

(51) Int. Cl.
  *A61D 17/00* (2006.01)
  *G01K 13/00* (2006.01)
  *A61B 5/00* (2006.01)
  *G01K 1/02* (2006.01)
  *A61B 5/11* (2006.01)
  *A61B 5/145* (2006.01)

(52) U.S. Cl.
  CPC ............ *G01K 13/002* (2013.01); *G01K 13/004* (2013.01); *A61B 5/1112* (2013.01); *A61B 5/145* (2013.01); *A61B 2503/40* (2013.01); *A61B 2560/0209* (2013.01)

(56) References Cited

U.S. PATENT DOCUMENTS

| | | | |
|---|---|---|---|
| 6,664,897 B2 | 12/2003 | Pape et al. | |
| 6,773,405 B2 | 8/2004 | Fraden et al. | |
| 6,868,804 B1 * | 3/2005 | Huisma et al. | 119/842 |
| 7,026,941 B1 | 4/2006 | Anderson | |
| 7,164,361 B2 | 1/2007 | Poliska | |
| 7,467,603 B2 * | 12/2008 | Davies | 119/712 |
| 7,690,141 B2 * | 4/2010 | Steinfort et al. | 40/301 |
| 7,705,736 B1 * | 4/2010 | Kedziora | 340/573.3 |
| 7,918,185 B2 * | 4/2011 | Araki et al. | 119/174 |
| 2002/0010390 A1 | 1/2002 | Guice et al. | |
| 2002/0154015 A1 | 10/2002 | Hixson | |
| 2003/0137431 A1 | 7/2003 | Hogan | |
| 2004/0233971 A1 | 11/2004 | Meads et al. | |
| 2006/0155172 A1 * | 7/2006 | Rugg | 600/300 |
| 2007/0008150 A1 * | 1/2007 | Hassell | 340/573.1 |
| 2007/0103296 A1 | 5/2007 | Paessel et al. | |
| 2008/0312511 A1 | 12/2008 | Osler et al. | |
| 2009/0187392 A1 | 7/2009 | Riskey et al. | |
| 2010/0160809 A1 | 6/2010 | Laurence et al. | |
| 2010/0261981 A1 | 10/2010 | Griffioen | |
| 2011/0251514 A1 | 10/2011 | Fults et al. | |
| 2013/0197323 A1 * | 8/2013 | Rettedal | A01K 11/007 600/302 |

* cited by examiner

REMOTE MONITORING SYSTEMS

RELATED APPLICATIONS

This application is a National Phase of International Application Number PCT/US2012/066962 filed Nov. 29, 2012 and claims the benefit of U.S. Provisional Application 61/565,357, filed Nov. 30, 2011, the entire contents of which are incorporated herein by reference.

FIELD OF THE INVENTION

The present invention provides systems for remotely monitoring sensors, particularly systems for remotely monitoring the temperature of subject animals.

BACKGROUND OF THE INVENTION

During the last 25 years many Western countries have witnessed substantial changes in the roles of veterinarians working in dairy cattle practice. Until the 1970s, the emphasis of their work was on the treatment of individual, clinically diseased animals, and it was only when the farmer decided a particular cow needed attention that he would call out his practitioner—it was an era of passive veterinary attention.

In the early 1970s, however, things began to change. Herd fertility schemes were introduced, first in the UK and Australia, and shortly afterwards in other Western countries. They represented a turning point in veterinary services offered to the dairy farmer. Their introduction was due mainly to a dramatic increase in the average size of dairy herds—an attempt by farmers to increase labor productivity at a time when economic margins between income and costs were decreasing—but which resulted in far less time being spent attending to individual cows. Consequently, many problems arose, but in particular related to health and fertility.

Towards the end of the 1990s further developments in dairy cattle practice took place in some Western European countries, Australia and North America. The protocol used for herd health programs consisted of three core elements: (1) the routine monitoring of animals, farm conditions, farm management and farm data, (2) the analysis of problems and the identification of impending problems, (3) the introduction of preventative actions. For a practitioner to carry out the task of "monitoring" he or she must easily and rapidly be able to identify when specific signs and symptoms in the animals or farming system deviate from an acceptable, preset norm. When monitoring animals a number of parameters are assessed. In all cases, the focus is on the early identification and tracking of deviations from a predetermined range of target figures, and on providing farmers with basic information relating to their animals' performance.

Monitoring in these systems was executed in one of three ways: as a general inspection of the farm and animals, by assigning a score to individual animals, or through epidemiological surveys that generate a probability figure. Examples of these different approaches may be found in the literature. Most noticeably, the late 1990s were recognized as a time when risk management became a more prominent issue on the dairy farm.

A common problem with these systems is the difficulty in monitoring large herds and also great inconsistencies when monitoring is based on human observation. A number of automated systems for monitoring parameters associated with health and fertility, such as temperature, have been proposed. Examples include those found in the following patents and publications: 2010/0261981; U.S. Pat. No. 6,773,405; 2002/0010390; 2008/0312511; 2002/0154015; U.S. Pat. No. 6,113,539; U.S. Pat. No. 7,164,361; 2002/0010390; U.S. Pat. No. 7,026,941; U.S. Pat. No. 6,664,897; 2010/0160809; 2009/0187392; 2003/0137431; and 2004/0233971.

These systems suffer several general drawbacks. First, data transmission from the systems is unreliable and difficult to implement in barn and feedlot environments. Second, many of the systems rely on RFID technology which requires that specialized equipment needs to be installed in close proximity to the animals being monitored. Third, the temperatures sensors themselves are unreliable and not general suitable for use in large scale.

SUMMARY OF THE INVENTION

Figure 1:
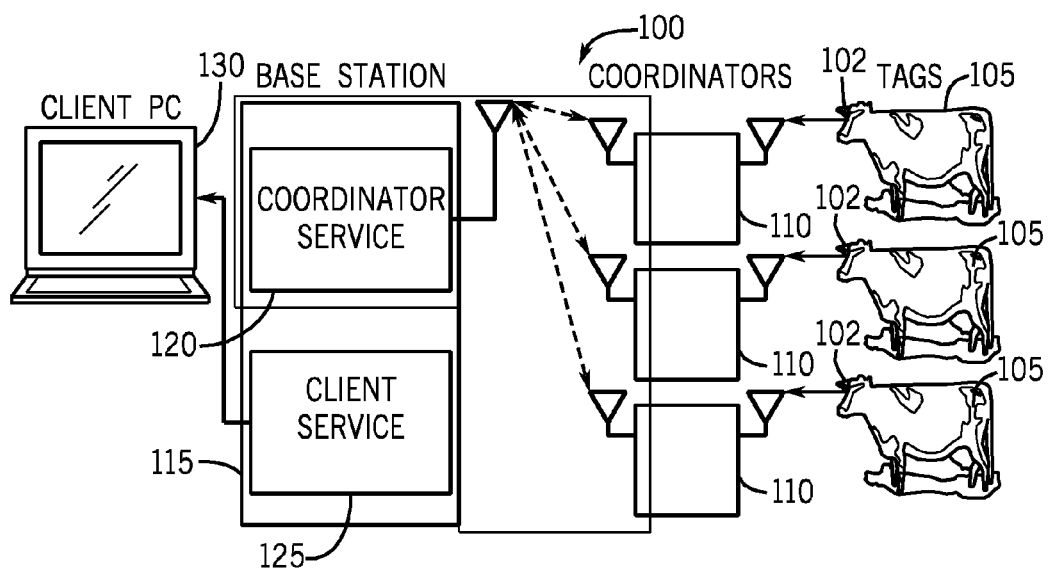
FIG. 1 provides a schematic depiction of a system of the present invention.

The present invention provides systems for remotely monitoring sensors, particularly systems for remotely monitoring the temperature of subject animals.

In some embodiments, the present invention provides systems comprising: a plurality of sensors configured to transmit data on a low power and/or short range transmission link; one or more coordinators in wireless communication with the sensors, the coordinators configured to convert signals received via the low power and/or short range transmission link to a longer range transmission link; and a base station in wireless communication with the one or more coordinators via the longer range transmission link so that data generated by the sensors is transferred to the base station via the coordinators. In some embodiments, the low power and/or short range transmission link utilizes a 802.15.4 signal. In some embodiments, the longer range link is selected from the group consisting of a cellular network and a transmission link using a 802.11 protocol. In some embodiments, the system is configured so that only one sensor is transmitting data to the coordinator at any given time. In some embodiments, the sensor is selected from the group consisting of time sensors, temperature sensors, humidity sensors, magnetic field sensors, voltage sensors, current sensors, noise sensors, pressure sensors, electrical switches, biological sensors, pH sensors, motion sensors, chemical sensors, pathogen sensors, bacteria sensors, strain gauges, ultra violet sensors, proximity sensors, flow rate sensors, gas sensors, imaging devices, accelerometers, and gyroscopes.

In some embodiments, the present invention provides systems comprising: a plurality of tags affixable to an animal, the tags configured to transmit data to a coordinator on a low power and/or short range transmission link; one or more coordinators in wireless communication with the tags, the coordinators configured to convert signals received via the low power and/or short range transmission link to a longer range transmission link; and a base station in wireless communication with the one or more repeater stations via the longer range transmission link so that data generated by the tags is transferred to the base station via the coordinators. In some embodiments, the low power and/or short range transmission link utilizes a 802.15.4 protocol. In some embodiments, the longer range transmission link utilizes a 802.11 protocol. In some embodiments, the tags comprise one or more sensors that generate data to be transferred to the coordinators. In some embodiments, the sensor is a temperature sensor. In some embodiments, the temperature sensor is a tympanic membrane temperature sensor. In some embodiments, the tag is in communication with one or more sensors that generate data to be transferred to the coordinators. In some embodiments, the sensor is a temperature sensor. In some embodiments, the base station is configured to analyze temperature data received from the temperature sensors via the coordinators to identify characteristics of sick animals or animals in estrus and alert the user of the system to specific individuals that are showing these characteristics. In some embodiments, the system is configured so that only one tag is transmitting data at any given time to the coordinator.

In some embodiments, the present invention provides a tag affixable to an animal comprising a temperature sensor; a housing enclosing components to translate, read and store temperature data received from the temperature sensor; a low power/short range transmitter configured to transmit the temperature data; and visual indicator capable of being remotely activated. In some embodiments, the temperature sensor is a tympanic sensor that extends from the housing on a flexible shaft.

In some embodiments, the present invention provides a tag affixable to an ear of an animal comprising: a male component comprising a temperature sensor and a housing enclosing components to translate, read and store temperature data received from the temperature sensor; a low power/short range transmitter configured to transmit the temperature data; and visual indicator capable of being remotely activated, the housing having extending therefrom two stems, each stem comprising a head at its distal end; and a female component comprising two bosses, wherein the bosses are positioned to receive a head from one of the stems so that the male component may be securely attached to the female component in the ear of the animal. In some embodiments, the temperature sensor is a tympanic sensor that extends from the housing on a flexible shaft.

In some embodiments, the present invention provides methods of monitoring a desired subject comprising: providing a system as described above; associating the sensors with desired subjects; and monitoring at least one parameter of the desired subjects via the base station.

In some embodiments, the present invention provides methods of monitoring the temperature of a plurality of animals comprising: providing a system as described above associating the tags with the plurality of animals; and monitoring the temperature of the plurality of animals via the base station.

In some embodiments, the present invention provides methods of identifying an animal in need of treatment in a herd of animals comprising: monitoring the temperature of a plurality of animals via a temperature sensor system; and identifying animals in need of treatment, wherein a core body temperature change of greater than 1.5 degrees F. in an individual animal in a six to 24 hour period is indicative of a disease. In some embodiments, the core body temperature change is corrected for changes in ambient temperature. In some embodiments, the core body temperature change is greater than 2.0 degrees F. In some embodiments, the disease is Bovine Respiratory Disease.

DETAILED DESCRIPTION OF THE INVENTION

The present invention provides systems for remotely monitoring a variety of sensors. The systems preferably comprise a plurality of sensors configured to transmit data to a coordinator on a low power and/or short range radio frequency link. The sensors may be used to provide data on a variety of parameters which are described in more detail below. The one or more coordinators are preferably in wireless communication with the sensors. The coordinators are configured to convert signals received via the low power and/or short range transmission radio frequency link to a longer range transmission link. A base computing station is preferably in communication with the one or more coordinators via the longer range transmission link. In some preferred embodiments, the low power and/or short range radio frequency link transmission utilizes an IEEE 802.15.4 protocol. In some preferred embodiments, the longer range transmission link utilizes an IEEE 802.11 Wi-Fi signal of various frequencies or a cellular network. In some preferred embodiments, the system is configured so that only one sensor is transmitting data at any given time (time slotting) in order to reduce data packet loss due to packet collisions.

The present system finds use with a variety of sensors and devices, including, but not limited to, the following: time sensors, temperature sensors, humidity sensors, magnetic field sensors, voltage sensors, current sensors, noise sensors, pressure sensors, electrical switches, biological sensors, pH sensors, motion sensors, chemical sensors, pathogen sensors, bacteria sensors, strain gauges, ultra violet sensors, proximity sensors, flow rate sensors, gas sensors, imaging devices, accelerometers, and gyroscopes and combinations of two or more such sensors.

In some embodiments, the remote monitoring systems of the present invention are used to monitor a physical parameter such as temperature in an animal. One preferred embodiment of the present invention is depicted schematically in FIG. 1. Referring to FIG. 1, the systems 100 preferably comprises a plurality of tags 102 affixed to animals 105. In preferred embodiments, the tags are in wireless communication with one or more coordinators 110. In preferred embodiments, the wireless communication between the tags and coordinators 110 is via a short range radio frequency link (data). The coordinators 110 are preferably in turn in wireless communication with a base station 115.

In preferred embodiments, the wireless communication between the coordinators 110 and the base station 115 is via a longer range radio frequency link signal. Thus, one function of the coordinators 110 is to wirelessly communicate with the tags and convert their short range radio frequency link (data) into a longer range radio frequency link signal and transmit that data through a wireless fidelity (Wi-Fi) network to the base station 115. In some embodiments, the coordinator timestamps the data if timestamping was not received from the tag and compiles the data along with other sensor tag data within range. In further embodiments, the coordinator is programmed to run an algorithm to determine when to periodically transmit data through the long range radio antenna to the base station.

The base station 115 preferably comprises a computer that provides a coordinator service 120 and a client service 125. In preferred embodiments, the coordinator service is responsible for responding to service requests from coordinators in the system and is preferably implemented as a socket sever running on the base station. The coordinator service is preferably configured to listen for TCP connections on specified ports.

The client service 125 preferably provides an interface with a client device, such as a computer 130, through wireless communication. Other suitable client devices include, but are not limited to mobile computing devices such as PDAs and tablet computers as well as cellular devices. The base station preferably comprises software that can store and analyze the data for a plurality (e.g., tens, hundreds or thousands) of individual tags simultaneously. In preferred embodiments, the software provides for analysis of body temperature data using algorithms that are designed to expose characteristics of irregularities of the health status of animals and alert the user of the system to specific individuals that are showing these characteristics. The software preferably further provides automated alert notices to mobile computing devices such as a PDA, tablet computer or a cellular device in the form of an e-mail or text message or other suitable messaging format.

In some embodiments, the coordinators are configured to establish a connection with the base station. In further embodiments, once the connection is established, the coordinator is the master and directs all communications. Accordingly, the coordinator is configured to transmit commands to the coordinator service. After transmission of a command, the coordinator service is configured to transmit an acknowledgement to the coordinator if the command has been successfully transmitted and a non-acknowledgment if there is a failure. In some preferred embodiments, the coordinator is configured to ensure tag data is transferred to the base station and to synchronize internal data with the rest of the system.

The coordinator is preferably configured to issue a variety of commands to the system, including, but not limited to request join commands, tag data reports, request counts, tag activation report, request time sync, tag command report, request new tag list, request tag command list, response form a, request coordinator pending data, and coordinator data report. The request join command is issued by a coordinator wanting to join the network and receive setup parameters. The coordinator is preferably aware of the network SSID, password, and TCPIIP parameters in order to successfully issue this command. Upon receipt of this command, the base station determined if the coordinator has been registered with the system. If so, an acknowledge response (ACK) with the assigned parameters is generated. Otherwise, a non-acknowledge (NAK) response is generated.

The tag data report is issued by the coordinator to report a temperature sample from a tag. The data accompanying the command includes a data packet comprising one or more of the following parameters: tag identification, time, temperature reading (e.g., tympanic temperature reading), ambient temperature, link quality for the received coordinator message as measured by the tag, link quality for data transmission s measured by the coordinator, number of attempts needed to transmit data from tag to coordinator, and tag battery capacity remaining. The base station adds a new sample record to the animal currently carrying the specified tag containing the desired data. An ACK response is then generated by the base station. Duplicate records are acknowledged, but not stored.

The request count command is issued by the coordinator to request the number of new tags waiting to be activated by the system and the number of tags with commands waiting to be delivered. Upon receipt of this command, the base station will send the current counts. The coordinator then utilizes these counts to request the actual data immediately afterward. The tag activation command is issued by the coordinator to indicate that a tag has been assigned a specified timeslot and should be removed from the new tags list. The request time sync command is issued by the coordinator to request the current time. The tag command report command is issued by the coordinator to indicate that a tag has accepted the specified command and should be removed from the tag commands list. The request new tag list command is issued by the coordinator to request any subset of the new tag list. The request tag command list command is issued by the coordinator to request any subset of the tag command list. The request coordinator pending data command is issued by the coordinator to request any pending data. The coordinator data command is issued by the coordinator to send status information, preferably battery capacity remaining and other data concerning the operation of the coordinator.

The systems of the present invention, including tags, coordinators and base station, are preferably configured to provide the maximum coverage area for the tags being monitored. In some embodiments, the coordinators are arranged in a pattern that will provide for a desired level of coverage. In some embodiments, the coordinators are programmed to allow mesh networking with each other in order to extend coverage or improve the range of the Wi-Fi signal to the base station. Data from individual tags is preferably forwarded by coordinators via the path of best signal quality to adjacent beacons or directly to the base station.

In some embodiments, the systems further provide protocols for determining the location of a tag (and associated animal). In these embodiments, triangulation from multiple coordinators is utilized by software resident in the base station to determine a quadrant where the tag is located to allow the user to begin the search for the tag in the general area of its location. By using a plurality of coordinators in the field, the system can determine the sensors approximate location based on the signal level readings to each coordinator. Coordinators may speak directly to the base station or relay information to/from nearby coordinators to/from the base station.

In some embodiments of the present invention, the remote monitoring systems comprise a tag that is fixable to the body of an animal. The tags of the present invention preferably comprise a sensor that provides data on a parameter such as temperature of the animal. In some embodiments, the sensor is a temperature sensor that is configured to measure the tympanic temperature of an animal or the temperature of the ear canal. Accordingly, in some embodiments, the tags of the present system comprise a temperature sensor element that extends from the tag so that it is inserted into a desired position in the ear of the animal when the tag is affixed to the ear of the animal. In some embodiments, the temperature sensor is located on the distal end a flexible shaft. In some embodiments, the temperature sensor is positioned so that the tympanic temperature of the animal can be taken. The tags further may preferably comprise a computer chip, an antenna for sending and/or receiving signals, and a power source. In preferred embodiments, these components are enclosed in a sealed or sealable weatherproof casing to protect the components from environmental elements such as rain, snow and dust. In further preferred embodiments, the tags comprise one or more visual indicators that may be activated by the system. Suitable visual indicators include, but are not limited to lights such light emitting diodes (LEDs). In some embodiments, the tags comprise visual indicators with one or more colors or signalling patterns such as blinking patterns.

Figure 2:
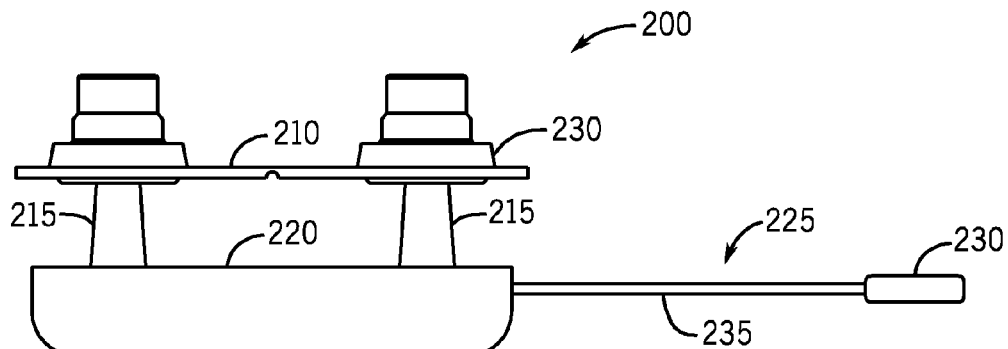
FIG. 2 provides a side view of a tag of the present invention.
Figure 3:
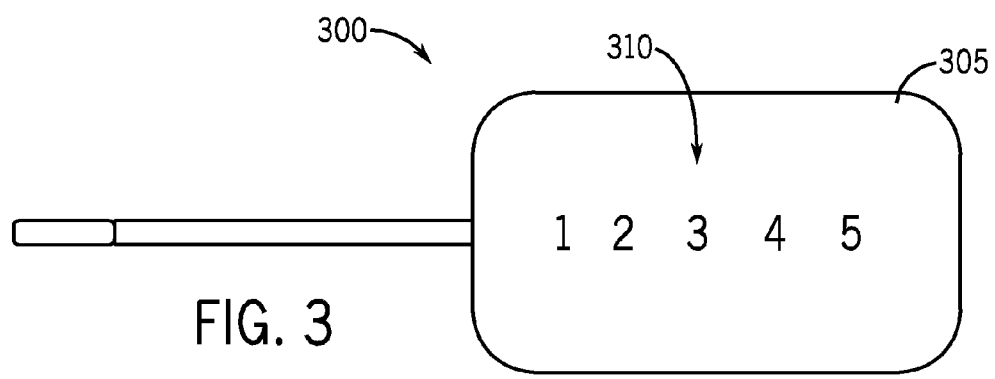
FIG. 3 provides a top view of a tag of the present invention.

In preferred embodiments, the tags of the present invention are fixable to an animal, preferably to the ear of an animal. Referring to FIG. 2, a tag 200 of the present invention preferably comprises a male component 205 and a female component 210. The male component 210 preferably comprises at least one stem 215 that projects from a face 220 of the male component 210. The stem 215 at its distal end includes a head (not shown) that is engageable with the female component 210 to securely attach the tag to the ear of the animal. In some embodiments, the head incorporates a hard insert material as is known in the art. In further embodiments, a pin of an applicator tool is insertable through a hollow bore (not shown) in the stem 215 to engage with the hard insert to apply a driving force to the hard insert. In some embodiments, the tag 200 further comprises a sensor 225 (e.g., a temperature sensor) that extends from the male component 205. The sensor 225 preferably comprises a sensor element 230 at the end of a shaft 235. The shaft 235 is preferably flexible. FIG. 3 provides a top view of a tag 300 of the present invention. In some embodiments, the male component 305 further comprises indicia 310 that are visible to a user. In some embodiments, the indicia may be a number or lettering system as is known in the art. In further preferred embodiments, the indicia is one or more remotely activateable visual indicators (e.g., an LED) that is visible so that the visual indicator may be observed by a user examining the tag or an animal displaying the tag.

Referring again to FIG. 2, the female component 210 preferably comprises at least one boss component 230 which receives the head of the male component 210 in a snap locking arrangement so that the head is retained within the boss. The boss preferably comprises at least one peripheral flange located at of adjacent to one end thereof. This is the end though which the head is forced through an opening. The further comprises an internal cavity accessible through the opening that is shaped to receive the head of the male component. The wall defining the opening preferably comprises a number of projections that engage the head so that one the head has been forced through the opening into the cavity the head is engaged so that the head may not be withdrawn through the opening.

A variety of other methods are known in the art for fixing tags to the ear of an animal and are within the purview of the present invention.

In preferred embodiments, the male components 205 of the present invention comprise two stem and head arrangements that correspond to two boss arrangements on the female component 210. This dual arrangement allows the tag to be fixed to the ear of the animal in a desired orientation so that the sensor 225 is correctly positioned in the ear of the animal (e.g., the sensor extends into the ear so that the distal end of the sensor is adjacent to the tympanum.

Figure 4:
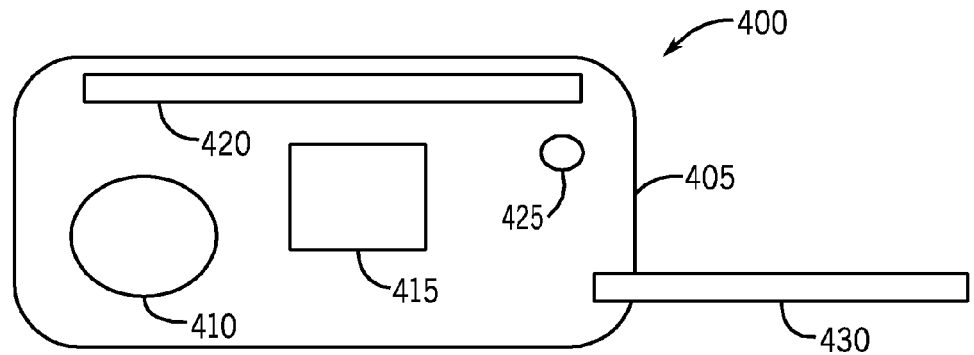
FIG. 4 provides a schematic depiction of a tag of the present invention.

A schematic depiction of the male component 400 of a tag of the present invention is provided in FIG. 4. The male component 400 preferably comprises an external housing 405. The external housing 405 is preferably waterproof or weather resistant. In some embodiments, the external housing 405 is formed from a top portion and bottom portion that can be permanently or reversibly engaged to provide a weatherproof or weather resistant enclosure. In some embodiments, the male component 400 comprises a power source 410 (e.g., a battery), computer chip 415, antenna 420 and an RF transmitter/receiver that are enclosed in the external housing 405. In some embodiments, the male component 400 further comprises one or more visual indicators 425 (e.g., an LED) that is visible on the external housing 405 so that the visual indicator 425 may be observed by a user examining the tag or an animal displaying the tag. The visual indicator(s) are preferably remotely activateable via wireless communication with the base station and coordinators described above. In some embodiments, the user can choose to turn the visual indicator on or off using via the use device or the visual indicator may be turned on or off automatically by the base station if a particular parameter (e.g., elevate temperature) is met. In some embodiments, the male component 400 further comprises a sensor 430 (e.g., a temperature sensor) that extends from the external housing 405.

Accordingly, in preferred embodiments, the tags of the present invention comprise a water proof enclosure including a RF transmitter/receiver, temperature probe and power source. These components work in conjunction to take the body temperature of an animal and transmit that and other vital information to a base station via a coordinator. The tags may also be preferably programmed to send signal strength to the coordinators as well as remaining battery power.

Figure 5:
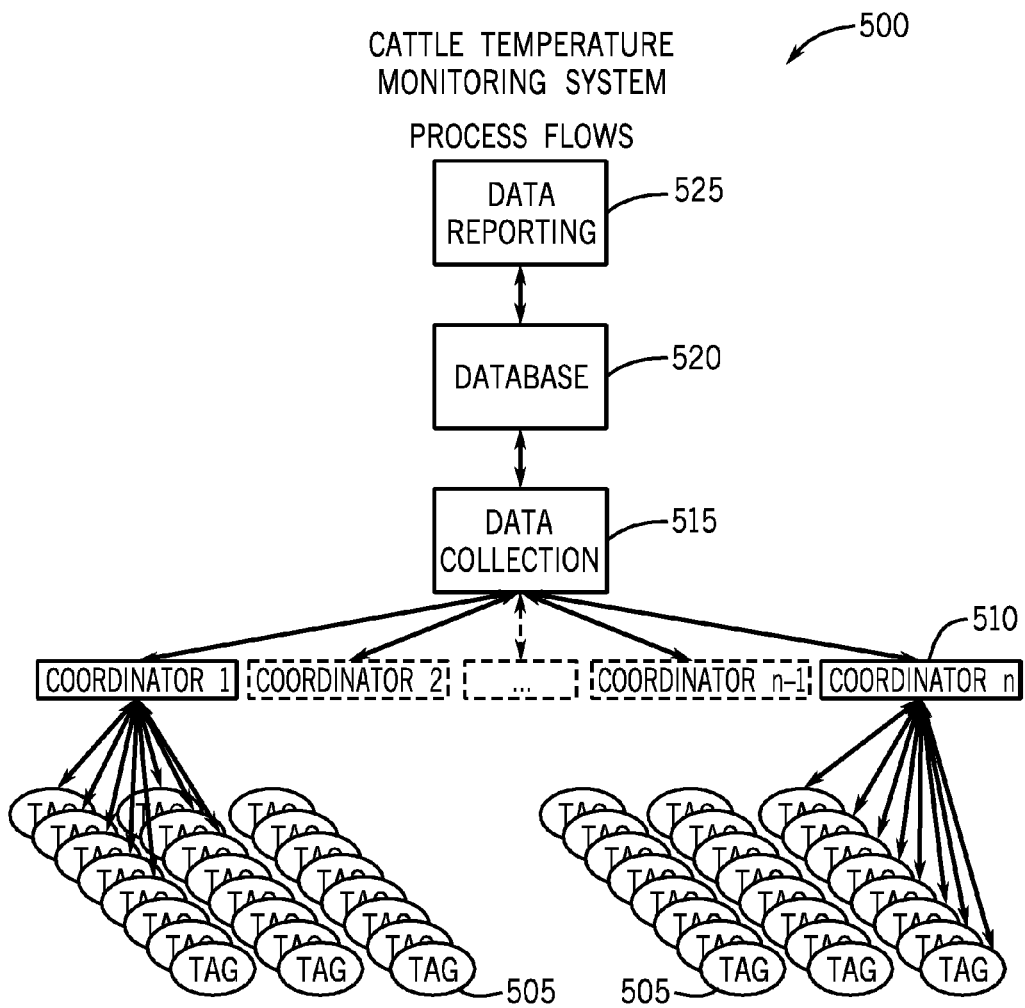
FIG. 5 provides a schematic of the process flow of the present invention.

A schematic of the process flow 500 of the present invention is provided in FIG. 5. Referring to FIG. 5, a plurality of tags 505 are in wireless communication with one or more coordinators 510. Data is collected 515 from the coordinators 505 and organized in a database 520. The data may then be reported 520 through any suitable user interface. As described above, the individual tags will be affixed to one ear of the animal with a thermistor probe protruding out of the tag housing and going into the ear canal of the animal coming into close proximity of the tympanic membrane. The tag comprises electronic circuitry inside the housing of the tag with components to translate, read, store, and transmit the temperature data from the thermistor to the coordinators. The visual indicator on the tag is capable of being turned on (e.g., continuous or blinking signal) by the base station for a predetermined period of time with the intent of making location of the tag easier to locate in the field. Such "locate" actions are needed in the event of an irregularity in the system and/or tag, such as elevated temperature or low power remaining in the tag.

The tags of the present invention comprise a programmable computer chip and are preferably preprogrammed for convenient operation. In preferred embodiments, the tags operate in one of 3 distinct modes: factory initialization, shelf sleep mode, and active mode.

With respect to factory initialization, following the connection of the battery to the device, the device will be powered in active mode for a predetermined period of time (e.g., about 10 minutes) during which time it will undergo a testing/initialization program comprising one r more of the following steps: a. Update internal FLASH memory with the latest code version; b. Assign unique MAC number, ID code, and other personalization information; c. Perform calibration of the Temperature measuring device; d. Connect to Functional test repeater and perform send/receive test, while measuring RF communication parameters; e. Measure and report remaining battery capacity; and f. Transition to shelf life sleep mode.

With respect to shelf sleep mode, the tags are programmed during factory initialization to wake up after a predetermined time interval and listen for a beacon signal. If a beacon signal is been detected and it contains the correct sequence code associated with the tag system, the tag notifies the network controller that it is available to join. The tag awaits approval by the network, but if approval is denied or network responds with the wrong handshaking code, it will go back to sleep for the predetermined time interval. If no beacon is detected, the tag measures its probe temperature and calculates the minimum/maximum storage temperatures. The tag stores the values in onboard FLASH memory and will go back to sleep for the predetermined time interval.

With respect to the active mode, if the base station has allowed the tag to join the network the tag is assigned a specific time slot and several "make up time slots" and the tag is placed in an active mode of operation. In active mode, the tag is programmed to perform one or more of the following steps: a. Wake up after a predefined time interval coincident to its programmed time slot; b. Take a temperature measurement; c. Verify the channel is clear to transmit and transmit the data to the system controller; d. Wait for transmit acknowledge and if OK go to sleep for the predefined time interval; and e. If no transmit acknowledge is received, wait for make up time slot and try transmission again.

In some embodiments, the tags are programmed to store multiple time-stamped temperature data points but only send them out occasionally at a predetermined time slot. The system does not burden the coordinators or the tags with a mesh-network type of set-up where data is daisy-chained to the base station randomly through the tags themselves. A mesh network in this situation would severely limit battery life because tags would be constantly transmitting data back and forth. In preferred embodiments of the present invention, the tags communicate directly to a coordinator using a low power/short range radio frequency link (e.g., a 802.15.4) via a time slotting program so that only one tag is transmitting data at any given time. In preferred embodiments, time slotting is controlled using beacons on the 802.15.4 protocol which allows for synchronous time slotting between all of the tags. This system reduces data packet loss due to packet collisions (as in a mesh network) and enhances battery life. The coordinator then sequences all data it receives and delivers it to the base station via a longer range amplified Wi-Fi antenna (e.g., 802.11) which does not interfere with the 802.15.4 frequency range. The "transfer" of data first through a low power and/or short range radio frequency link and then through a longer range high antenna directivity radio frequency link provides significant advantages over previously described systems. In some embodiments, data may be sent immediately to the coordinator if a data point is outside of a predetermined range (or based on algorithm placed on the chip in the tag).

In some embodiments, the present invention provides a core body temperature tag system. In some embodiments, the systems comprise ambient temperature sensors. The ambient temperature sensors are preferably in communication with the coordinators and the data received from the ambient temperature sensors is used to determine temperature trends. In some embodiments, the system is configured to tabulate temperature ranges, preferably in real time. Indoor and outdoor temperature ranges may be calculated. In preferred embodiments, the system tabulates temperature readings from tags in the system. Based on the number of active tags in the system, the average temperature is calculated in real-time as new temperature data from tags enters the system. It is contemplated that this system accounts for changes in ambient temperature (e.g., increases in ambient temperature leading to increases in animal temperature) that effect animal temperature. This in turn allows reduction of false positives (i.e., animals identified with abnormally high temperatures). Examples of the calculations for determining the temperature ranges follow:

(Total Temperatures)/(Total number of tags in Outdoor)=Average Max Temp Outdoors (Total Temperatures)/(Total number of tags in Indoor)=Average Max Temp Indoors.

In some embodiments, the systems are configured to take the temperature humidity index (THI) into account. The THI provides an indication of whether the ambient temperature and humidity will have an effect on the animals using standard THI tables. In some embodiments, the system alerts the user that based on the THI, the system may give false readings with regard to elevated animal temperatures.

In some embodiments, this system monitors and transmits periodic temperature data of the tympanic membrane of cattle to a computing system that can alert the user of the system to irregularities in body temperature that may indicate sickness, periods within the estrus cycle, and parturition. In some embodiments, the accumulated data to determine/predict the estrus cycle of a female animal. In preferred embodiments, the system is configured to analyze the temperature data to determine trends related to, for example, sickness, estrus or physical activity, so that false positive may be eliminated.

Accordingly, the present invention may be used in monitoring the current state of health for a large group of animals. In some embodiments, the present invention notifies a user of a particular animal's (e.g., a cow, horse, sheep, pig or other subject animal) current state of health and assists in locating a particular animal. Temperature fluctuations are often a harbinger of health change (e.g., infection, respiratory disease, infectious contagious intestinal disease, bacterial infection, viral infection, fungal infection) for animals. Via an algorithm, the system of the present invention integrates both a particular animal's identity and that particular animal's core body temperature over an extended period of time (e.g., weeks). In some embodiments, the algorithm determines a temperature trend for the particular cow over an extended period of time (e.g., temperature trend from completion of last estrus). In other embodiments, the algorithm determines an average temperature for the particular cow over a period of time (e.g., temperature average from last estrus). In further embodiments, upon integration, the algorithm provides for comparison of the particular animal's temperature information (e.g., temperature trend or average) with a standardized animal's temperature fluctuation information upon entry into particular health changes (e.g., infection, respiratory disease, infectious contagious intestinal disease, bacterial infection, viral infection, and fungal infection). In other embodiments, upon integration, the algorithm provides for comparison of the particular animal's temperature information (e.g., temperature trend or average) with previous temperature fluctuations for that particular animal. If a particular animal's temperature fluctuations indicate the animal is entering, exiting, or not experience a change in health state, the algorithm provides a notification to the user and also may activate the visual indicator on the tag. The individual animal may be located by the user so that action (e.g., treatment or veterinary examination) may be undertaken.

In some embodiments, the present invention provides methods of identifying an animal in need of treatment in a herd of animals comprising monitoring the temperature of a plurality of animals via a temperature sensor system and identifying animals in need of treatment. In some embodiments, the identified animals are then treated, for example by administering an antibiotic. In some embodiments, the core body temperature change is measured by a tympanic temperature sensor. In some embodiments, a core body temperature change of greater than 1.4, 1.5, 1.6, 1.7, 1.8, 1.9, 2.0. 2.1, or 2.2 degrees Fahrenheit is indicative of disease. In some embodiments, a core body temperature change of greater than 1.4, 1.5, 1.6, 1.7, 1.8, 1.9, 2.0, 2.1, or 2.2 degrees Fahrenheit over a time period of from 4 to 8 hours, 4 to 12 hours, 6 to 12 hours, 6 to 24 hours or 12 to 24 hours is indicative of disease. In some embodiments, the core body temperature change is corrected for changes in ambient temperature. In some embodiments, the disease is Bovine Respiratory Disease.

The present invention may also be used in maintaining an animal's reproduction (e.g., estrus) schedule for a large group of animals. Via an algorithm, the system of the present invention integrates both a particular animal's identity and that particular animal's core body temperature over an extended period of time (e.g., weeks). In some embodiments, the algorithm determines a temperature trend for the particular animal over an extended period of time (e.g., temperature trend from completion of last estrus). In other embodiments, the algorithm determines an average temperature for the particular animal over a period of time (e.g., temperature average from last estrus). In further embodiments, upon integration, the algorithm provides for the comparison of the particular animal's temperature information (e.g., temperature trend or average) with standardized animal temperature fluctuation information upon entry into estrus. In other embodiments, upon integration, the processor compares the particular animal's temperature information (e.g., temperature trend or average) with previous temperature fluctuations for that particular animal. If a particular animal's temperature fluctuations indicate the cow is entering, exiting, or not in estrus, the algorithm provides a notification to the user and also may activate the visual indicator on the tag. The individual animal may be located by the user so that action (e.g., segregation from herd, mating) may be undertaken.

The present invention is contemplated as a tool for preventive medicine. As such, the present invention may be used to create various databases of information (e.g., temperature trends) based upon a large group of animals. Such databases may be used to monitor the health status of a particular animal, and upon an indicative event (e.g., entrance into estrus, infection), a user may initiate appropriate intervention (e.g., breeding, infection treatment, segregation). The present invention further permits the accumulation of temperature trends for an entire herd of animals, and the integration and interpretation of such information. Over an extended period of time (e.g., months) numerous animals within a herd will develop forms of infection. A processor equipped with algorithms and a database may be used to integrate and process temperature trend information for animal which developed forms of infection. The processing of this information permits the development of a database aimed at predicting an animal's propensity for developing a particular form of infection based upon a comparison of a particular animal's temperature trends with the database. In preferred embodiments, databases are created aimed at predicting the development of numerous forms of infection (e.g., infection, respiratory disease, infectious contagious intestinal disease, bacterial infection, viral infection, fungal infection). In further embodiments, infection databases may be used with different herds of animals in a similar preventive medicine capacity.

The present invention also contemplates the development of databases aimed at predicting an animal's estrus state. Over an extended period of time (e.g., months) numerous animals within a herd will enter and exit estrus. A processor equipped with algorithms and a database may integrate and process temperature trend information for animals which enter and exit estrus. The processing of this information permits the development of a database aimed at predicting an animal's propensity for entering estrus. In further embodiments, estrus databases may be used with different herds of animals in a similar capacity.

In further embodiments, the systems of the present invention are utilized for food monitoring. Perishable food monitoring is utilized to ensure that temperature does not rise or fall outside of a certain level, or humidity does not rise or fall outside of a certain level for an extended period of time. Using low powered sensors, the data is sent from the tag to the coordinator. The data is then sent via the coordinator through a long distance radio to a central office or a base station. The advantage of this system over existing technology is that it can actively transmit the temperature data in real-time and can track both temperature and time duration at, above, or below a set limit. Current technology only gives a visual indication of past events (such as food in transit saw elevated temperature at some point during shipping).

A number of sensors may used with the systems of the present invention. In some embodiments, one or more of following sensors can be added to the system application: temperature sensor (low powered sensor that is kept around the food to monitor temperature); photo sensor (to detect light if container has been opened); magnetic sensor (using a magnet latch to detect if door have been opened or tampered); motion sensor (detects if there was movement inside the freight vehicle); accelerometer (detects if any product may have been damaged due to rough handling during shipping); and biosensors (detection of a chemical or substance that combines a biological component with a physicochemical detector).

In further embodiments, the present invention provides systems for freight monitoring. As freight is being transported, it is important to report tamper evidence to a central location where this data can be monitored. Using the low power sensor network, tags within a container or affixed to the outside of a container, preferably so that entry is not possible unless the tag is removed or otherwise compromised, relay a signal if any tampering with the container or tag has occurred back to a database at an office location through a high speed wireless connection such as a network similar to that of a cellular phone system. The advantage over existing technology is that this system is capable of actively notifying a user if and when tampering is taking place (or took place). The following sensors can be added to the system application: photo sensor (to detect light if doors have been opened); temperature sensor (if a temperature controlled container has been opened); magnetic sensor (using a magnet latch to detect if door have been opened or tampered); motion sensor (detects if there was movement inside the freight vehicle); electronic circuit (interrupted/broken when tampering takes place).

In further embodiments, the present invention provides systems for asset tracking/inventory management. This application can be used to track location/condition of parts or equipment. The systems find use in warehouses to track containers, bins, pallets, products, or even equipment such as forklift trucks by monitoring signal strength from sensors to various coordinators. This application can also be used to track shipping containers when they leave a facility and arrive at a new facility. The sensor is placed on the equipment piece, pallet or container and contains a GPS chip or using multiple coordinators in the area, the position can be tracked using the signals from a plurality of coordinator devices to triangulate the location. Another application is to place a coordinator in a trailer or cab of a semi-truck which is connected to a GPS unit. The tags transmit data such as temperature and gyroscopic information via the low power RF signal and the coordinator combines this data with the GPS data and sends it out over a long range wireless network such as a cellular network to a central database.

By putting motion detection sensors such as an accelerometer or gyroscope the type of movement or forces exerted on the asset can be determined. For example the acceleration/deceleration of a forklift can be determined. This would be useful to verify usage habits of equipment. Also fragile or sensitive product can be monitored using these sensors as a quality check to verify whether or not a product or asset experienced rougher than acceptable handling conditions during fabrication and/or transport.

EXAMPLES

Example 1

The tympanic temperature tags of the present invention were field tested and compared to vaginal temperature measurement. Briefly, tags (approximately 24) were installed into cow's ears to collect temperature data for approximately 1 month. A predetermined number of tags (8) were removed after 8 days to compare the readings from the tympanic temperature with a vaginal core body temperature using a Hobo device. The remaining tags were left in for additional observations. The following observations were made: ambient temperatures were collected, algorithms for use in measuring temperature for sickness were developed, irritation from thermister was assessed, behavior from the weight of the tags was assessed, and retention of the tags was assessed.

The thermister was small enough to enter the cow's ear canal without any apparent problems. Pulling on the ear away from the animal allowed the ear canal to open up and the thermister was easily inserted into the ear canal. Once the tags were installed, the cows did not exhibit any irritation or infections on the ear or in the ear canal. The weight of the tag did not cause ear drooping. The tags were not removed by dislodgement by the cow or from chewing by other cows.

Figure 6:
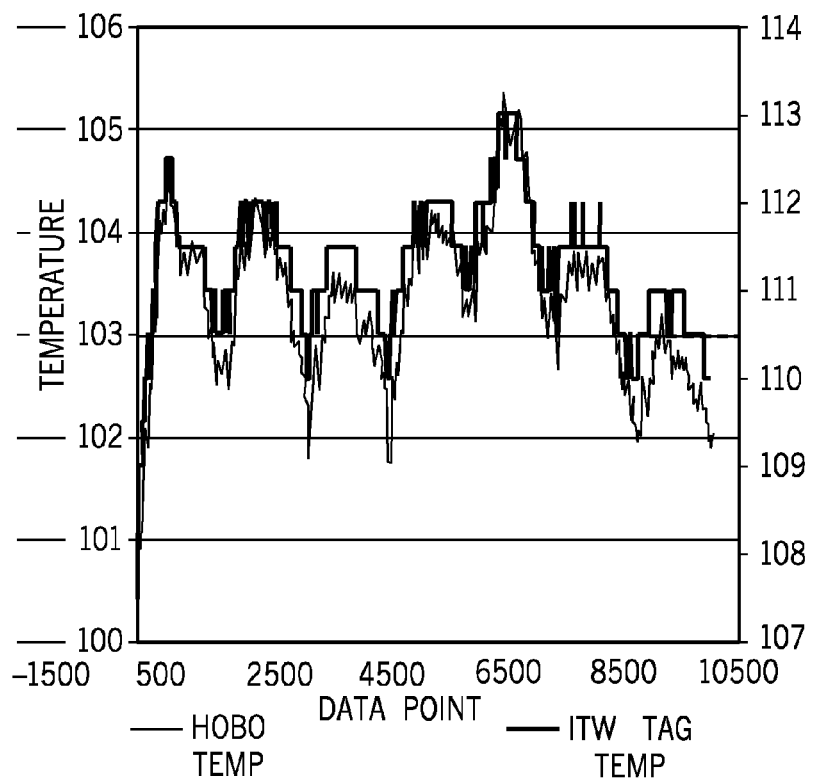
FIG. 6 provides a graph depicting the correlation of temperatures determined by a tag of the present invention as compared to a hobo vaginal device.
Figure 7:
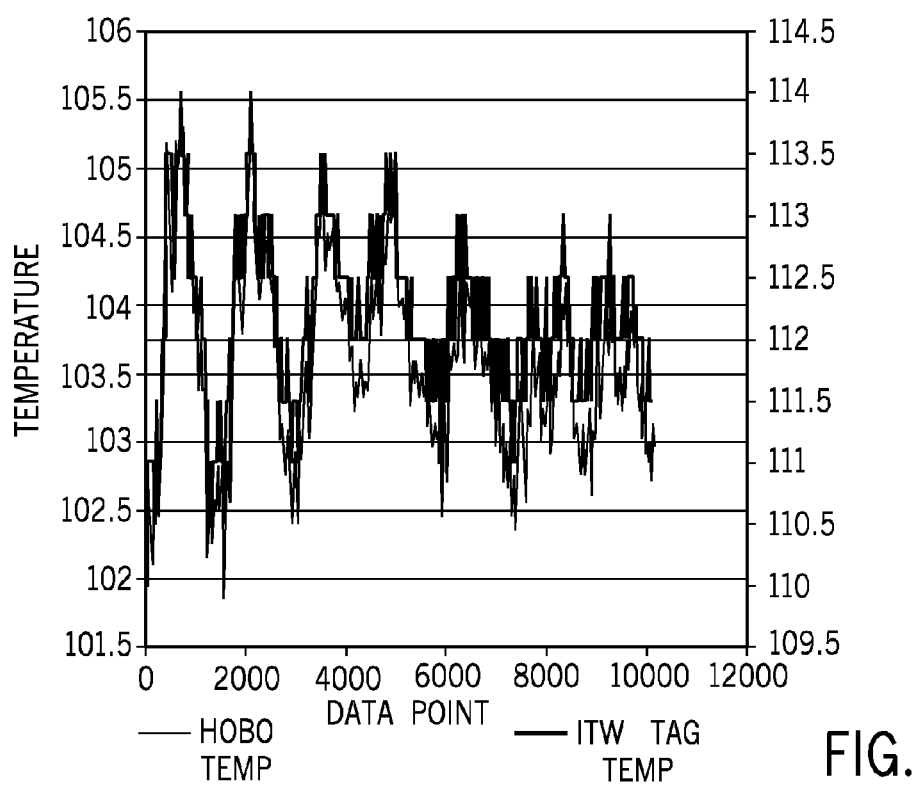
FIG. 7 provides a graph depicting the correlation of temperatures determined by a tag of the present invention as compared to a hobo vaginal device.
Figure 8:
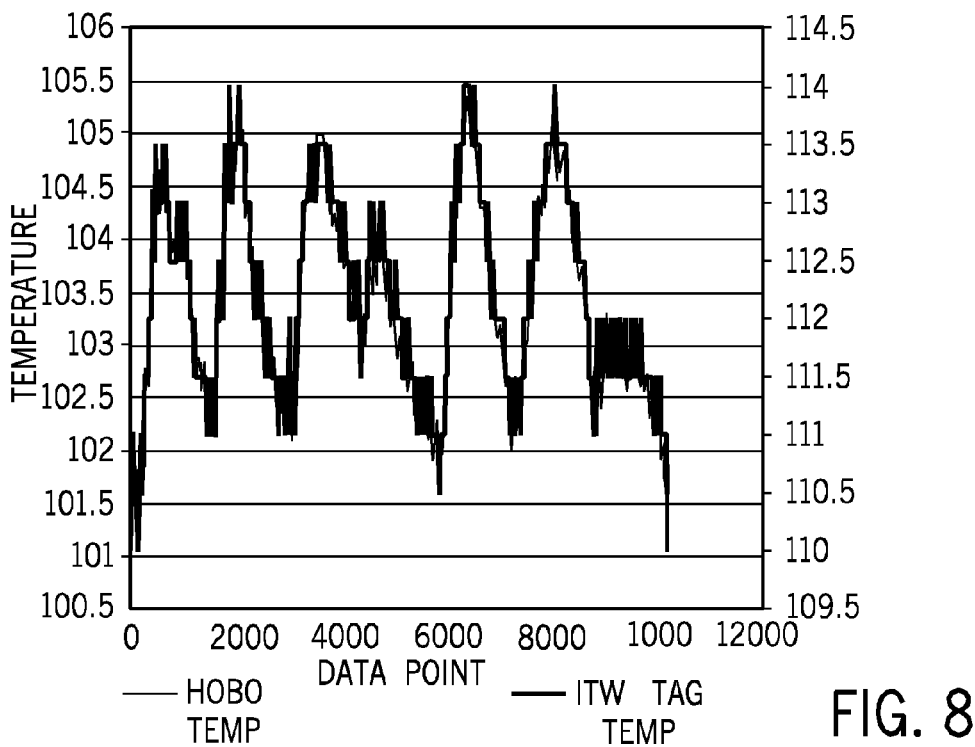
FIG. 8 provides a graph depicting the correlation of temperatures determined by a tag of the present invention as compared to a hobo vaginal device.

Temperature measurement via the tympanum was surprisingly well-correlated with temperature measurement by vaginal hobo device. As seen in FIGS. 6, 7, and 8 the temperature trends for two representative animals are identical to the hobo devices and with the calculation of the offset the temperature data is within 0.2 degrees of a vaginal temperature from the hobo device.

Figure 9:
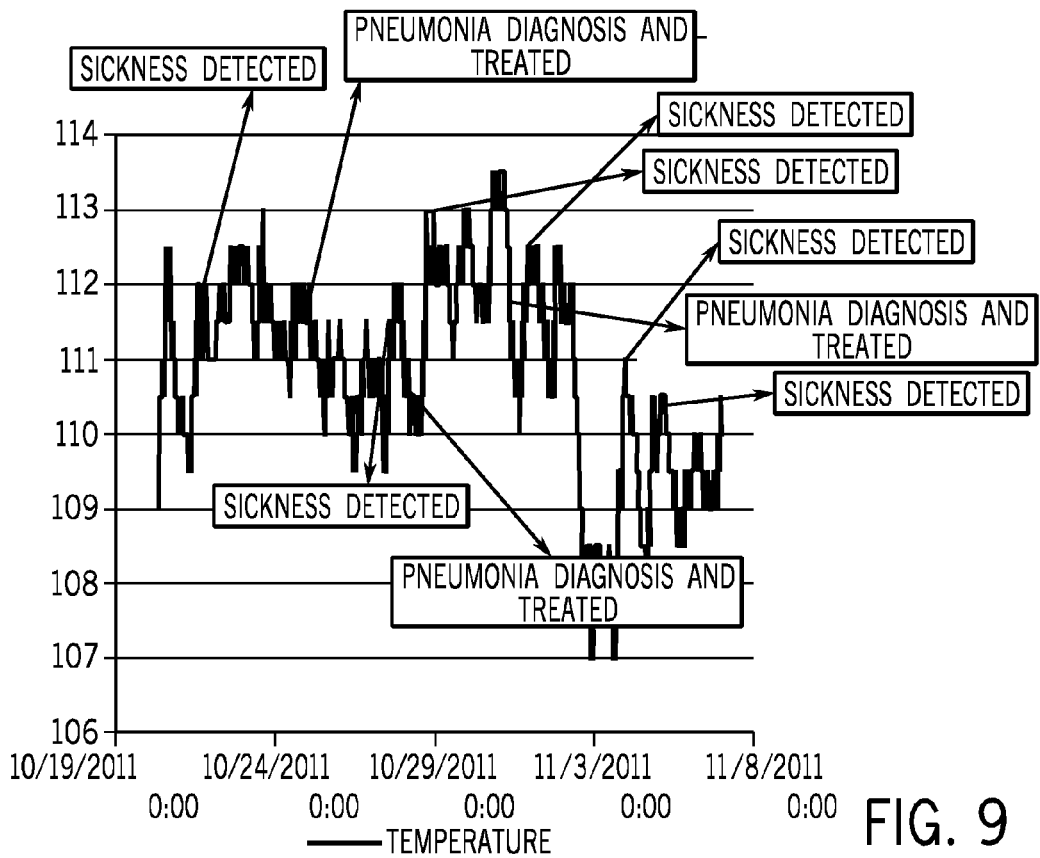
FIG. 9 provides a chart demonstrating the relationship of measured temperature to sickness in an individual cow.

Using tabulated data provided by Kansas State University, it was possible to correlate when a cow was diagnosed as being sick as well as the diagnosis and treatment of that cow. FIG. 9 shows cow tag number 18 that was diagnosed and treated several times with pneumonia. As can be seen, a rapid decrease in body temperature of from about 1.5-2.0 degrees F. followed by a rapid increase in temperature of greater than 2.0 degrees F. is a sign of onset of sickness. After the treatment was administered, the temperature began to level out.

Example 2

In a separate trial, cow tag number 16 exhibited from the very beginning of the trial possible illness based on the large temperature swings. For the first two days, temperature recordings show significant swings in the core body temperature of +/−2.0 degrees F. through the course of the day. Based on this observation and prior testing, this is an indication of possible illness on the animal. After consulting with the veterinarian, the initial temperature changes were caused by a side effect of sweating from a vaccine which was administered during the installation of the core body temperature tag. However, on day three a significant temperature spike continued. On day four, the veterinarian pulled the animal from the pen and the animal was diagnosed with BRD (Bovine Respiratory Disease) and treated. The temperature swing continued through the next day and then steadily got smaller on day 6-7.

Example 3

In the same trial as Example 2, cow tag number 18 exhibited from the very beginning of the trial possible illness based on the large temperature swings. The initial temperature changes were attributed to vaccination. On the fourth day, a large swing in core body temperature was detected which is indicative of a possible illness. The next day that day the animal was pulled from its pen, diagnosed with BRD (Bovine Respiratory Disease), and treated.

The invention claimed is:

1. A system comprising:
    a plurality of sensors configured to transmit data on a low power and/or short range transmission link;
    a plurality of coordinators in wireless communication with said sensors,
    a base station in wireless communication with said plurality of coordinators via said longer range transmission link so that data generated by said sensors is transferred to said base station via said coordinators, said base station providing a coordinator service,
    said coordinators configured to 1) convert signals received via said low power and/or short range transmission link to a longer range transmission link, 2) issue a plurality of commands to the coordinator service and 3) direct communications from the base station to the sensor.

2. The system of claim 1, wherein said low power and/or short range transmission link utilizes a 802.15.4 signal.

3. The system of claim 1, wherein said longer range link is selected from the group consisting of a cellular network and a transmission link using a 802.11 protocol.

4. The system of claim 1, wherein said system is configured so that only one sensor is transmitting data to said coordinator at any given time.

5. The system of claim 1, wherein said sensor is selected from the group consisting of time sensors, temperature sensors, humidity sensors, magnetic field sensors, voltage sensors, current sensors, noise sensors, pressure sensors, electrical switches, biological sensors, pH sensors, motion sensors, chemical sensors, pathogen sensors, bacteria sensors, strain gauges, ultra violet sensors, proximity sensors, flow rate sensors, gas sensors, imaging devices, accelerometers, and gyroscopes.

6. The system of claim 5, wherein said system is configured so that only one tag is transmitting data at any given time to said coordinator.

7. The system of claim 1, wherein said plurality of coordinators are remote from an animal.

8. A system comprising:
    a plurality of tags affixable to an animal, the tags configured to transmit data to a coordinator on a low power and/or short range transmission link;
    a plurality of coordinators in wireless communication with said tags,
    a base station in wireless communication with said plurality of coordinators via said longer range transmission link so that data generated by said sensors is transferred to said base station via said coordinators, said base station providing a coordinator service, said coordinators configured to 1) convert signals received via said low power and/or short range transmission link to a longer range transmission link, 2) issue a plurality of commands to the coordinator service and 3) direct communications from the base station to the sensor.

9. The system of claim 8, wherein said low power and/or short range transmission link utilizes a 802.15.4 protocol.

10. The system of claim 8, wherein said longer range transmission link utilizes a 802.11 protocol.

11. The system of claim 8, wherein said tags comprise one or more sensors that generate data to be transferred to said coordinators.

12. The system of claim 11, wherein said sensor is a temperature sensor.

13. The system of claim 12, wherein said temperature sensor is a tympanic membrane temperature sensor.

14. The system of claim 12, wherein said base station is configured to analyze temperature data received from said temperature sensors via said coordinators to identify characteristics of sick animals or animals in estrus and alert a user of the system to specific individuals that are showing these characteristics.

15. The system of claim 8, wherein said tag is in communication with one or more sensors that generate data to be transferred to said coordinators.

16. The system of claim 15, wherein said sensor is a temperature sensor.

17. The system of claim 8, wherein said plurality of coordinators are remote from said animal.

18. A tag affixable to an animal comprising a temperature sensor; a housing enclosing components to translate, read and store multiple time-stamped temperature data points received from said temperature sensor and to transmit said multiple time-stamped temperature data points at a predetermined time slot; a low power/short range transmitter configured to transmit said temperature data to a plurality of coordinators in communication with a plurality of said tags and remote from said animal; and visual indicator capable of being remotely activated.

19. The tag of claim 18, wherein said temperature sensor is a tympanic sensor that extends from said housing on a flexible shaft.

20. A tag affixable to an ear of an animal comprising:
a male component comprising a temperature sensor and a housing enclosing components to translate, read and store multiple time-stamped temperature data points received from said temperature sensor and to transmit said multiple time-stamped temperature data points at a predetermined time slot; a low power/short range transmitter configured to transmit said temperature data to a plurality of coordinators remote from said animal; and visual indicator capable of being remotely activated, said housing having extending therefrom two stems, each stem comprising a head at its distal end; and a female component comprising two bosses, wherein said bosses are positioned to receive a head from one of said stems so that said male component may be securely attached to said female component in said ear of said animal.

21. The tag of claim 20, wherein said temperature sensor is a tympanic sensor that extends from said housing on a flexible shaft.

22. A method of monitoring a desired subject comprising:
providing a system according to claim 1;
associating said sensors with desired subjects; and
monitoring at least one parameter of said desired subjects via said base station.

23. A method of monitoring body temperature of a plurality of animals comprising:
providing a system according to claim 12;
associating said tags with said plurality of animals; and
monitoring the temperature of said plurality of animals via said base station.

24. A method of identifying an animal in need of treatment in a herd of animals comprising:
monitoring the temperature of a plurality of animals via the temperature sensor system of claim 12; and
identifying animals in need of treatment, wherein a core body temperature change of greater than 1.5 degrees F. in an individual animal in a six to 24 hour period is indicative of a disease.

25. The method of claim 24, wherein said core body temperature change is corrected for changes in ambient temperature.

26. The method of claim 24, wherein said core body temperature change is greater than 2.0 degrees F.

27. The method of claim 24, wherein said disease is Bovine Respiratory Disease.

* * * * *